US007930188B2

(12) United States Patent
Grasso et al.

(10) Patent No.: US 7,930,188 B2
(45) Date of Patent: Apr. 19, 2011

(54) COMPUTERIZED SYSTEM AND METHOD FOR GENERATING AN IMMUNIZATION SCHEDULE IN A HEALTHCARE ENVIRONMENT

(75) Inventors: Kay L Grasso, Kansas City, MO (US); Thomas C. Gifford, Kansas City, MO (US); J. Mark Hord, Richmond, MO (US); D. Allan Shoup, Kansas City, MO (US)

(73) Assignee: Cerner Innovation, Inc., Kansas City, MO (US)

( * ) Notice: Subject to any disclaimer, the term of this patent is extended or adjusted under 35 U.S.C. 154(b) by 1706 days.

(21) Appl. No.: 10/748,477

(22) Filed: Dec. 30, 2003

(65) Prior Publication Data
US 2005/0149352 A1    Jul. 7, 2005

(51) Int. Cl.
*G06Q 10/00* (2006.01)
*G06Q 50/00* (2006.01)
*A61B 5/00* (2006.01)
*G06F 19/00* (2006.01)

(52) U.S. Cl. .............................................. 705/2; 705/3
(58) Field of Classification Search .................. None
See application file for complete search history.

(56) References Cited

U.S. PATENT DOCUMENTS
6,985,870 B2 *  1/2006  Martucci et al. ................. 705/3

OTHER PUBLICATIONS

Miller et al. "Combining Tabular, Rule-Based, and Procedural Knowledge in Computer-Based Guidelines for Childhood Immunization" Computer and Biomedical Research 30, 211-231 (1997) Article No. CO971445.*
Swiech, Paul "All in One Shot", Dec. 15, 2003, the Pantagraph, Bloomington, Ill.*
Miller, Perry L., "Tools for Immunization Guideline Knowledge Maintenance" 1997, Computers and Biomedical Research 31, 172-189.*
Tang, Paul C., et al. "Measuring the Effects of Reminders for Outpatient Influenza Immunizations at the Point of Clinical Opportunity," Journal of the American Medical Informatics Association, vol. 6, No. 2, Mar./Apr. 1999.
Vaccine Check, www.vaccinecheck.com, "About the Program," 2003 Data Unit Corporation, Updated Jun. 29, 2003.
Office Action mailed Nov. 25, 2009 in U.S. Appl. No. 12/350,439.
Office Action mailed Jul. 15, 2010 U.S. Appl. No. 12/350,439.

* cited by examiner

*Primary Examiner* — Robert W Morgan
*Assistant Examiner* — Eliza Lam
(74) *Attorney, Agent, or Firm* — Shook, Hardy & Bacon L.L.P.

(57) ABSTRACT

A computerized method and system for generation an immunization schedule for a person in healthcare environment is provided. The system receives a request for an immunization schedule for a person and obtains information from an electronic medical record of the person stored within a comprehensive healthcare system. The system obtains one or more immunization schedules and utilizes the information from the electronic medical record of the person and the immunization schedule to generate a customized immunization schedule for the person. In another embodiment, the system receives immunization information for a person and stores the immunization information in the electronic medical record of the person within a comprehensive healthcare system.

19 Claims, 14 Drawing Sheets

COMPUTERIZED SYSTEM AND METHOD FOR GENERATING AN IMMUNIZATION SCHEDULE IN A HEALTHCARE ENVIRONMENT

CROSS-REFERENCE TO RELATED APPLICATIONS

Not applicable.

STATEMENT REGARDING FEDERALLY SPONSORED RESEARCH OR DEVELOPMENT

Not applicable.

TECHNICAL FIELD

The present invention relates generally to the field of computer software. More particularly, the invention relates to a computerized system and method for generating an immunization schedule in a healthcare environment.

BACKGROUND OF THE INVENTION

The Center for Disease Control (CDC) establishes guidelines for immunizations. According to the CDC, before the age of two, an infant will need 16 to 24 doses of vaccines. Children will need additional immunizations through adolescence. The CDC issues a schedule of recommended immunizations and recommended ages for vaccinations every year. Some diseases that children routinely receive immunizations for include: polio, measles, mumps, rubella, diphtheria, tetanus, whooping cough, meningitis, chicken pox, and hepatitis B. Currently immunizations are recorded on immunization cards kept by parents and guardians of the children. As such, many pieces of vital information regarding the immunizations for a child are not preserved.

What is needed is a system and method for storing immunization information for a patient and creating a dynamic patient-specific schedule for immunizations.

SUMMARY OF THE INVENTION

In one embodiment of the present invention, a computerized method and system for preventing one or more immunizations from being prematurely administered to a person is provided. The system receives the immunizations to be administered to a person and determines whether it is too soon to administer the immunization. And if so, the system outputs information that it is too early to administer the immunization.

In another embodiment of the present invention, a computerized method and system for preventing an inappropriate live virus combination from being administered to a person is provided. The system receives two or more live virus immunizations to be administered to a person and determines whether the two or more live virus immunizations constitute an inappropriate live virus combination. And if so, the system outputs information that the two or more live virus immunizations constitute an inappropriate live virus combination receiving two or more live virus immunizations to be administered to a person;

In yet another embodiment of the present invention, a computerized method and system for preventing adverse reactions to one or more immunizations to be administered to a person is provided. The system receives the immunizations to be administered and obtains healthcare information for the person. The system determines if the immunization is associated with an adverse reaction and if so, determines based on the healthcare information for the person if the person may have an adverse reaction to the immunization.

In still another embodiment of the present invention, a computerized method and system for generating an immunization schedule for a person is provided. The system receives a request for an immunization schedule for a person. The system obtains information from the person's electronic medical record stored within a comprehensive healthcare system and obtains one or more immunization schedules. Then the system utilizes the information from the electronic medical record and the immunization schedule to generate a customized immunization schedule for the person.

In yet another embodiment of the present invention, a computerized system and method for storing immunization information for a person is provided. The system receives immunization information for a person and stores the immunization information in the electronic medical record of the person within a comprehensive healthcare system.

BRIEF DESCRIPTION OF THE SEVERAL VIEWS OF THE DRAWINGS

The present invention is described in detail below with reference to the attached drawing figures, wherein:

FIG. 4 is a screenshot illustrating an exemplary implementation for displaying immunization information;

FIGS. 5-8 illustrate screenshots for entering immunization information in accordance with an embodiment of the invention;

FIG. 9 is a screenshot illustrating an exemplary implementation for displaying immunization information.

DETAILED DESCRIPTION OF THE INVENTION

Figure 1:
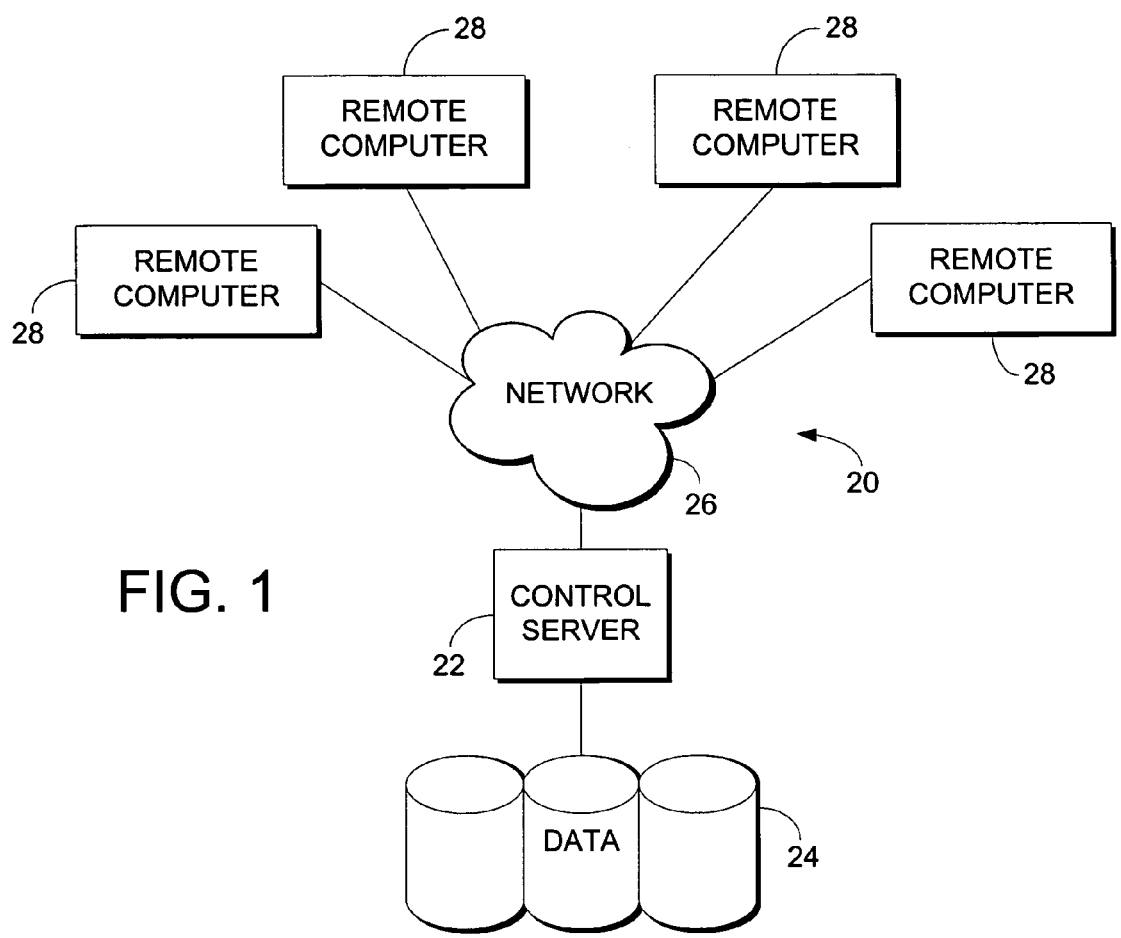
FIG. 1 is a block diagram of a computing system in accordance with an embodiment of the present invention.

The present invention provides a method and system for storing and displaying immunization information for a patient in a computing environment. FIG. 1 illustrates an example of a suitable medical information computing system environment 20 on which the invention may be implemented. The medical information computing system environment 20 is only one example of a suitable computing environment and is not intended to suggest any limitation as to the scope of use or functionality of the invention. Neither should the computing environment 20 be interpreted as having any dependency or requirement relating to any one or combination of components illustrated in the exemplary environment 20.

The invention is operational with numerous other general purpose or special purpose computing system environments or configurations. Examples of well-known computing systems, environments, and/or configurations that may be suitable for use with the invention include, but are not limited to, personal computers, server computers, hand-held, or laptop devices, multiprocessor systems, microprocessor-based systems, set top boxes, programmable consumer electronics, network PCs, minicomputers, mainframe computers, distributed computing environments that include any of the above systems or devices, and the like.

The invention may be described in the general context of computer-executable instructions, such as program modules, being executed by a computer. Generally, program modules include, but are not limited to, routines, programs, objects, components, data structures that perform particular tasks or implement particular abstract data types. The invention may also be practiced in distributed computing environments where tasks are performed by remote processing devices that are linked through a communications network. In a distributed computing environment, program modules may be located in both local and remote computer storage media, including memory storage devices.

With reference to FIG. 1, an exemplary medical information system for implementing the invention includes a general purpose computing device in the form of server 22. Components of server 22 may include, but are not limited to, a processing unit, internal system memory, and a suitable system bus for coupling various system components, including database cluster 24 to the control server 22. The system bus may be any of several types of bus structures, including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

Server 22 typically includes therein or has access to a variety of computer readable media, for instance, database cluster 24. Computer readable media can be any available media that can be accessed by server 22, and includes both volatile and nonvolatile media, removable and nonremovable media. By way of example, and not limitation, computer readable media may comprise computer storage media and communication media. Computer storage media includes both volatile and nonvolatile, removable and nonremovable media implemented in any method or technology for storage of information, such as computer readable instructions, data structures, program modules or other data. Computer storage media includes, but is not limited to, RAM, ROM, EEPROM, flash memory or other memory technology, CD-ROM, digital versatile disks (DVD), or other optical disk storage, magnetic cassettes, magnetic tape, magnetic disk storage, or other magnetic storage devices, or any other medium which can be used to store the desired information and which can be accessed by server 22. Communication media typically embodies computer readable instructions, data structures, program modules, or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media, such as a wired network or direct-wired connection, and wireless media such as acoustic, RF, infrared and other wireless media. Combinations of any of the above should also be included within the scope of computer readable media.

The computer storage media, including database cluster 24, discussed above and illustrated in FIG. 1, provide storage of computer readable instructions, data structures, program modules, and other data for server 22.

Server 22 may operate in a computer network 26 using logical connections to one or more remote computers 28. Remote computers 28 can be located at a variety of locations in a medical environment, for example, but not limited to, clinical laboratories, hospitals, other inpatient settings, a clinician's office, ambulatory settings, medical billing and financial offices, hospital administration, and home healthcare environments. Clinicians include, but are not limited to, the treating physician, specialists such as surgeons, radiologists and cardiologists, emergency medical technicians, physician's assistants, nurse practitioners, nurses, nurse's aides, pharmacists, dieticians, microbiologists, and the like. The remote computers may also be physically located in non-traditional medical care environments so that the entire healthcare community is capable of integration on the network. Remote computers 28 may be a personal computer, server, router, a network PC, a peer device, other common network node or the like, and may include some or all of the elements described above relative to server 22. Computer network 26 may be a local area network (LAN) and/or a wide area network (WAN), but may also include other networks. Such networking environments are commonplace in offices, enterprise-wide computer networks, intranets and the Internet. When utilized in a WAN networking environment, server 22 may include a modem or other means for establishing communications over the WAN, such as the Internet. In a networked environment, program modules or portions thereof may be stored in server 22, or database cluster 24, or on any of the remote computers 28. For example, and not limitation, various application programs may reside on the memory associated with any one or all of remote computers 28. It will be appreciated that the network connections shown are exemplary and other means of establishing a communications link between the computers may be used.

A user may enter commands and information into server 22 or convey the commands and information to the server 22 via remote computers 28 through input devices, such as keyboards, pointing devices, commonly referred to as a mouse, trackball, or touch pad. Other input devices may include a microphone, satellite dish, scanner, or the like. Server 22 and/or remote computers 28 may have any sort of display device, for instance, a monitor. In addition to a monitor, server 22 and/or computers 28 may also include other peripheral output devices, such as speakers and printers.

Although many other internal components of server 22 and computers 28 are not shown, those of ordinary skill in the art will appreciate that such components and their interconnection are well known. Accordingly, additional details concerning the internal construction of server 22 and computer 28 need not be disclosed in connection with the present invention.

Figure 2A:
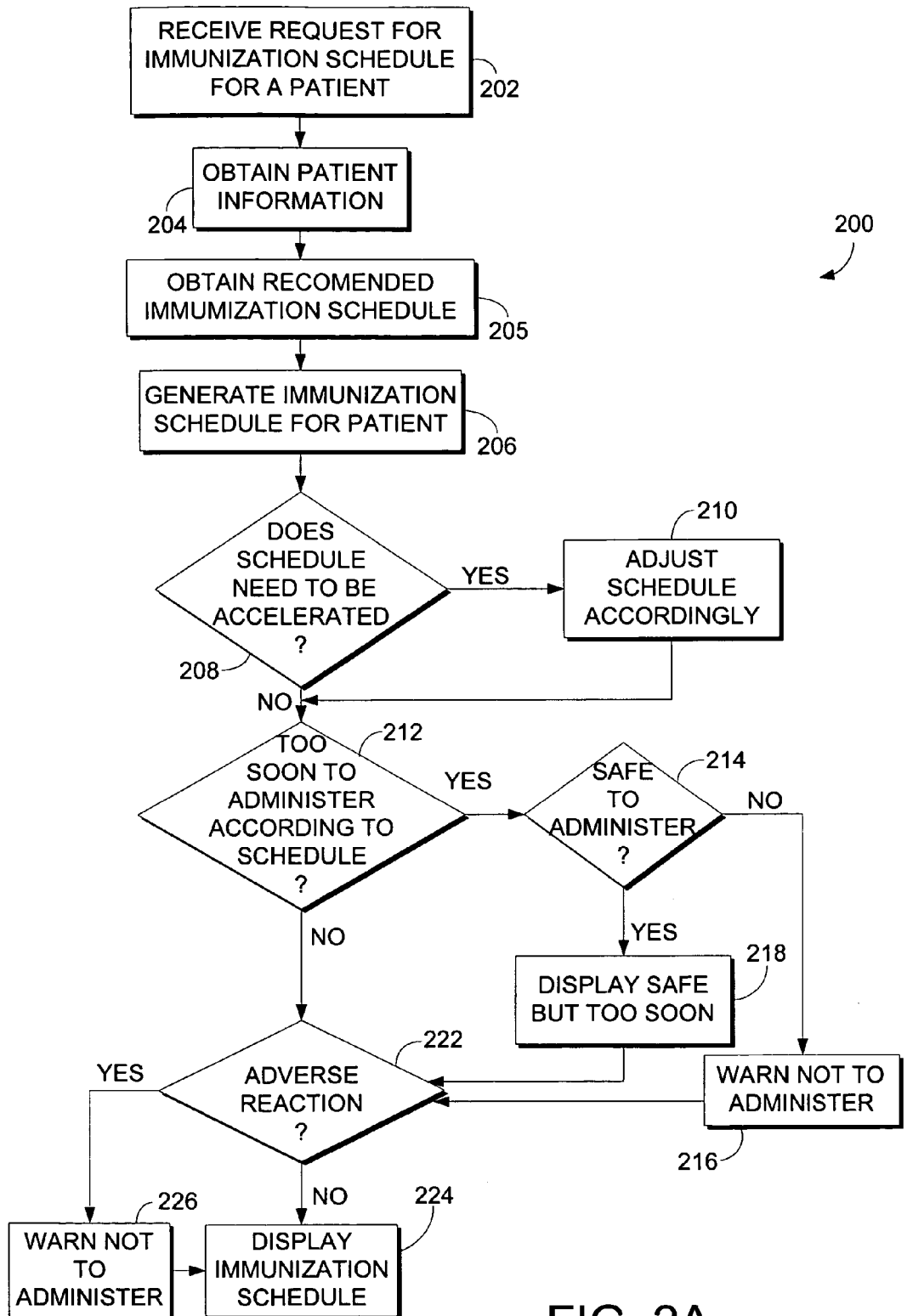
FIG. 2 is a flowchart representative of a computer program for displaying an immunization schedule for a patient in accordance with an embodiment of the present invention.

Although the method and system are described as being implemented in a WINDOWS operating system operating in conjunction with an Internet based system, one skilled in the art would recognize that the method and system can be implement in any system With reference to FIG. 2A, a method for displaying immunization information for a patient is provided. At block 202, the system receives a request for an immunization schedule for a patient. For example, the request may be from a clinician (or other user) before administering or documenting one or more immunizations or information related to immunizations for the patient. The request may also be received by another system or interface.

At block 204, the system obtains patient information for the patient. Patient information may be obtained in any number of ways, including from a database, table, and/or the patient's electronic medical record. Typically, patient information includes demographic information for the patient, documented information of immunizations given to the patient, allergy information, genetic information and the like.

At block 205, the system obtains a current recommended immunization schedule for children and adolescents. For example, the system may obtain the current CDC childhood immunization schedule. Alternatively, the recommended immunization schedule could be any applicable immunization schedule, for instance, a schedule for travel immunizations. One of skill in the art will appreciate that an immunization schedule may include any variety of immunizations and that immunizations are added and/or removed from recommended immunization schedule as technology and society change. Furthermore, the number of dosages of a particular vaccine and the timing of the immunization may also vary.

At block 206, the system utilizes the patient information and the immunization schedule to generate a custom immunization schedule for the patient. For example, the system uses any documented immunizations and the patient's age to determine when the next immunizations are due according to the recommended schedule. For example, based on the patient's age and documentation including that the patient has already had one immunization for Measles, Mumps and Rubella (MMR), the system may determine that the patient is due for a second MMR immunization.

At decision block 208, the system determines whether or not the patient's immunization schedule needs to be accelerated. For example, the system will determine whether the patient is overdue for receiving certain immunizations according to the recommended immunization schedule.

If the system determines that the patient's immunization schedule needs to be accelerated, at block 210 the system adjusts the schedule accordingly and the system proceeds to decision block 212. If the patient's schedule does not need to be adjusted the system proceeds to decision block 212. At decision block 212 the system determines whether or not it is too soon to administer one or more immunizations on the schedule for the patient. The system analyzes the patient's age, any information regarding the patient's prior immunizations and the recommended schedule to determine it is too soon to administer one or more of the immunizations.

If at decision block 212 the system determines it is too soon to administer one or more immunizations to the patient according to the schedule, at decision block 214 the system determines whether or not it is safe to administer one or more of the immunizations even though the immunization or immunizations are not due according to the schedule. For instance, the system may determine that it is safe to administer a second MMR immunization even though it premature according to the schedule. Or the system may determine that it is not safe to administer two MMR immunizations so closely together.

If the system determines it is not safe to administer the immunizations at decision block 214 the system warns the user not to administer the immunization(s) at block 216. The system may send a warning via a pop-up display or may place a flag by the immunization when the immunization schedule is displayed. The system then proceeds to decision block 222.

If the system determines that it is safe to administer the immunizations at decision block 214, the system indicates to the user that it is safe but too soon to administer the immunization at block 218, and proceeds to decision block 222. In one example, the system may warn the user by displaying a visual warning through a pop-up display or may place a flag by the immunization when the immunization schedule is displayed.

Figure 4:
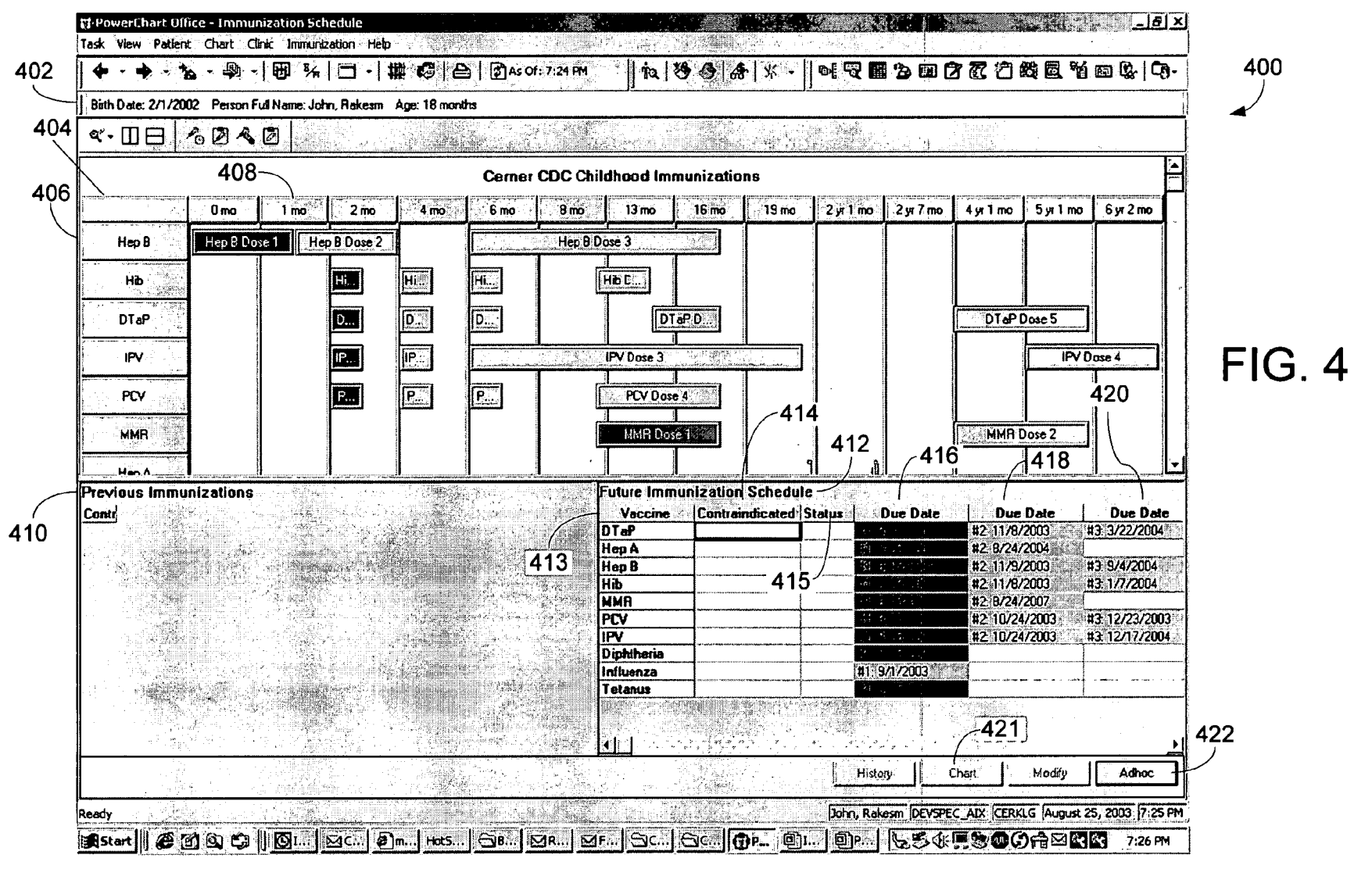
Figure 9:
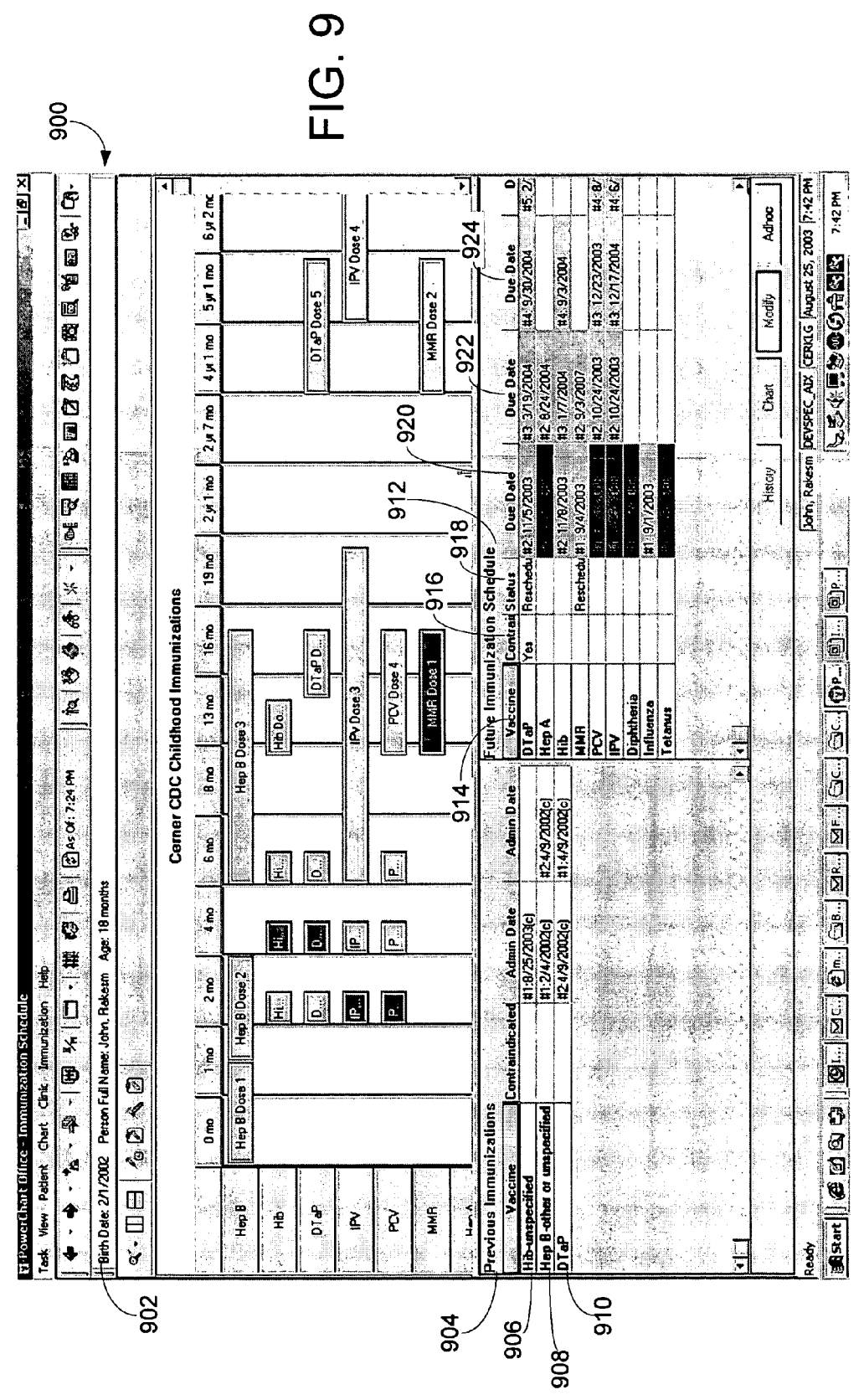

If at block 212 the system determines that it is not too soon according to the schedule to administer the immunization, the system proceeds to block 222. At decision block 222 the system determines whether any of the immunizations needed by the patient according to the customized immunization schedule would cause an adverse reaction. In one example, the system determines if the patient is taking a certain medication or has certain medical or genetic condition that would cause an adverse reaction to one or more of the immunizations. If so, at block 226 the system warns the user not to administer the immunization that may cause an adverse reaction and then proceeds to block 224 to display the immunization schedule. If at decision block 222 the system determines that the patient information does not indicate that an adverse reaction will occur, then the immunization schedule is displayed at 224. Exemplary immunization schedule displays are shown in FIG. 4 and FIG. 9 described below.

Figure 2B:
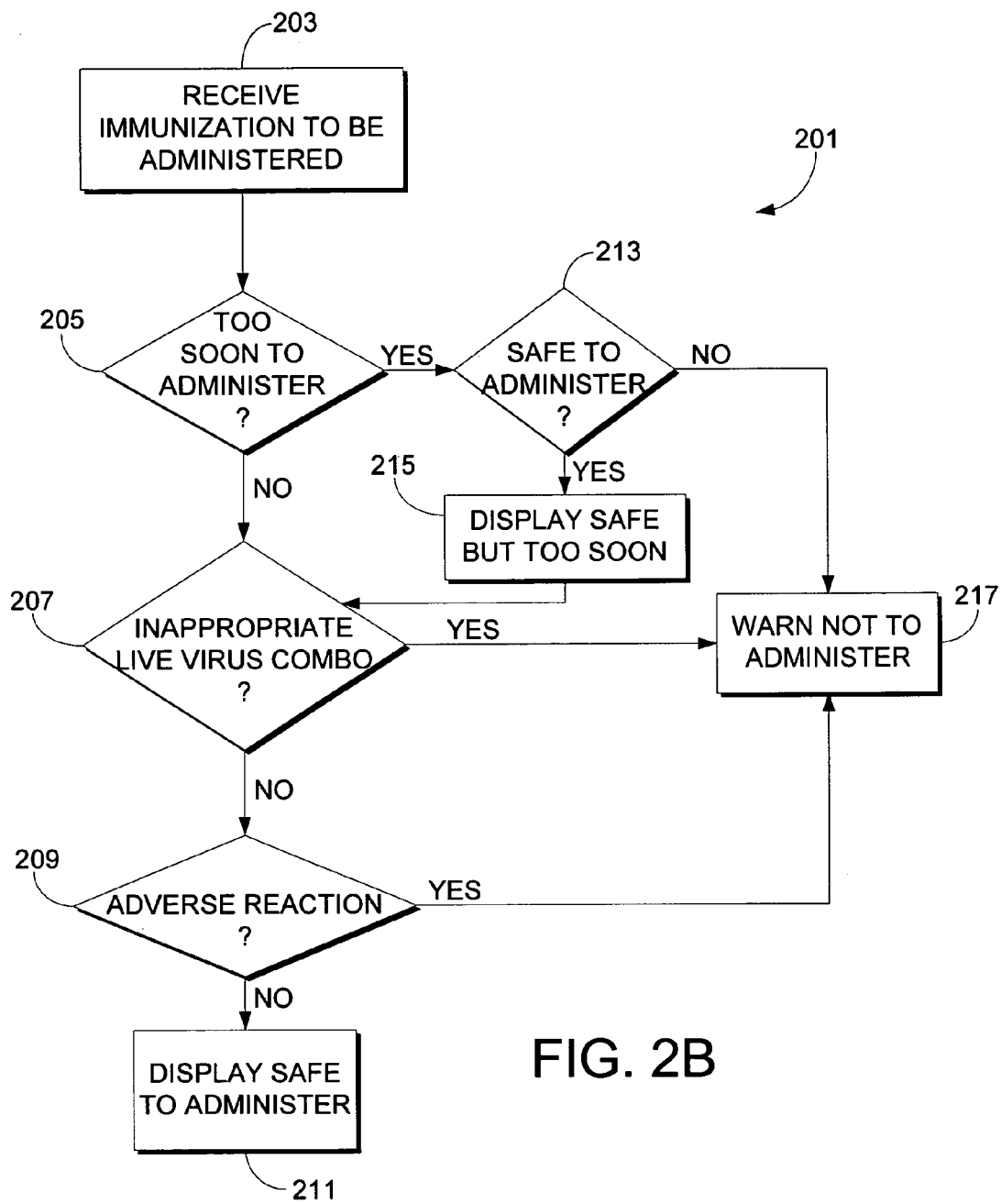

In one embodiment, decision blocks 212 and 222 of FIG. 2A are bypassed and the immunization schedule is displayed without any timing or adverse reaction analysis. This embodiment is shown in FIG. 2B. In this case, the system determines if the immunization are timely and whether warning for adverse reactions are needed after a user has entered the one or more immunizations that are going to be administered to the patient.

With reference to FIG. 2B, a system and method 201 is provided for determining whether immunization(s) are safe to administer to a patient. At block 203 the system receives the immunization(s) to be administered to the patient. The system may receive the immunizations to be administered to the patient from any number of sources. For example, the system could receive input directly from a healthcare provider or the immunizations may be received from another system or interface.

Then at decision block 205, the system determines whether it is too soon to administer any of the immunization(s) received at block 203. For example, as discussed above, it may be too soon to administer the second dose of an MMR immunization to a patient. The system can determine whether or not it is too soon to administer one or more immunizations by utilizing immunization information that has been recorded for the patient along with the recommended immunization schedule and any information regarding the safe timing of immunizations. This information may be obtained from a database, table or any other means known to those of skill in the art.

If the system determines that it is too soon to administer one or more of the immunization(s) to be administered, at decision block 213 the system determines whether it is safe to administer any of the immunizations. Again, the system uses information regarding the safe timing of immunizations to determine whether it is still safe to administer the immunization. If the system determines that it is safe to administer the one or more immunizations, at block 215 the system displays that it is safe but too soon to administer the one or more immunizations. The system then proceeds to decision block 207. If at decision block 213 the system determines that it is not safe to administer one or more of the immunizations, the system warns that it is not safe to administer the one or more of the immunizations at block 217.

Proceeding to decision block 207, if the immunizations to be administered to the patient are two or more live virus immunizations, the system determines whether the live virus immunizations constitute an inappropriate live virus combination. Again, the system can access information regarding what combinations of immunizations are inappropriate combinations and may endanger the well being of the patient. If at decision block 207 the system determines that the immunizations to be administered constitute an inappropriate live virus combination, at block 217 the system warns of the inappropriate combination and warns the user not administer the combination.

If at decision block 207, the system determines that the immunization(s) to be administered are not an inappropriate live virus combination, the system proceeds to decision block 209. At decision block 209, the system determines whether the immunizations may cause the patient to have an adverse reaction. In one example, the system determines that the patient is taking a certain medication or has certain allergy or genetic condition that would cause an adverse reaction to the immunization(s). The system preferably obtains patient information associations of patient information and immunizations indicative of adverse reactions from tables, databases and/or the patient's electronic medical record.

The patient information is compared to a list of medications, genetic information, allergies and other clinical information that are known to result in an adverse reaction to immunization(s). If the system determines that the patient may have an adverse reaction to one or more of the immunizations to be administered, the system warns the user not to administer the one or more immunizations. The system may also provide more information to the user regarding the potential adverse reaction.

If at decision block 209 the system determines that the patient information does not indicate that an adverse reaction will occur, the system indicates that it is safe to administer the immunization(s) at block 211. In one embodiment of the method and system of FIG. 2B, the system sends the user a message that it is safe to administer one or more of the immunizations. In another embodiment, the system does not display any messages. The omission of a warning would indicate to the healthcare provider that it is safe to administer the immunization.

Figure 3:
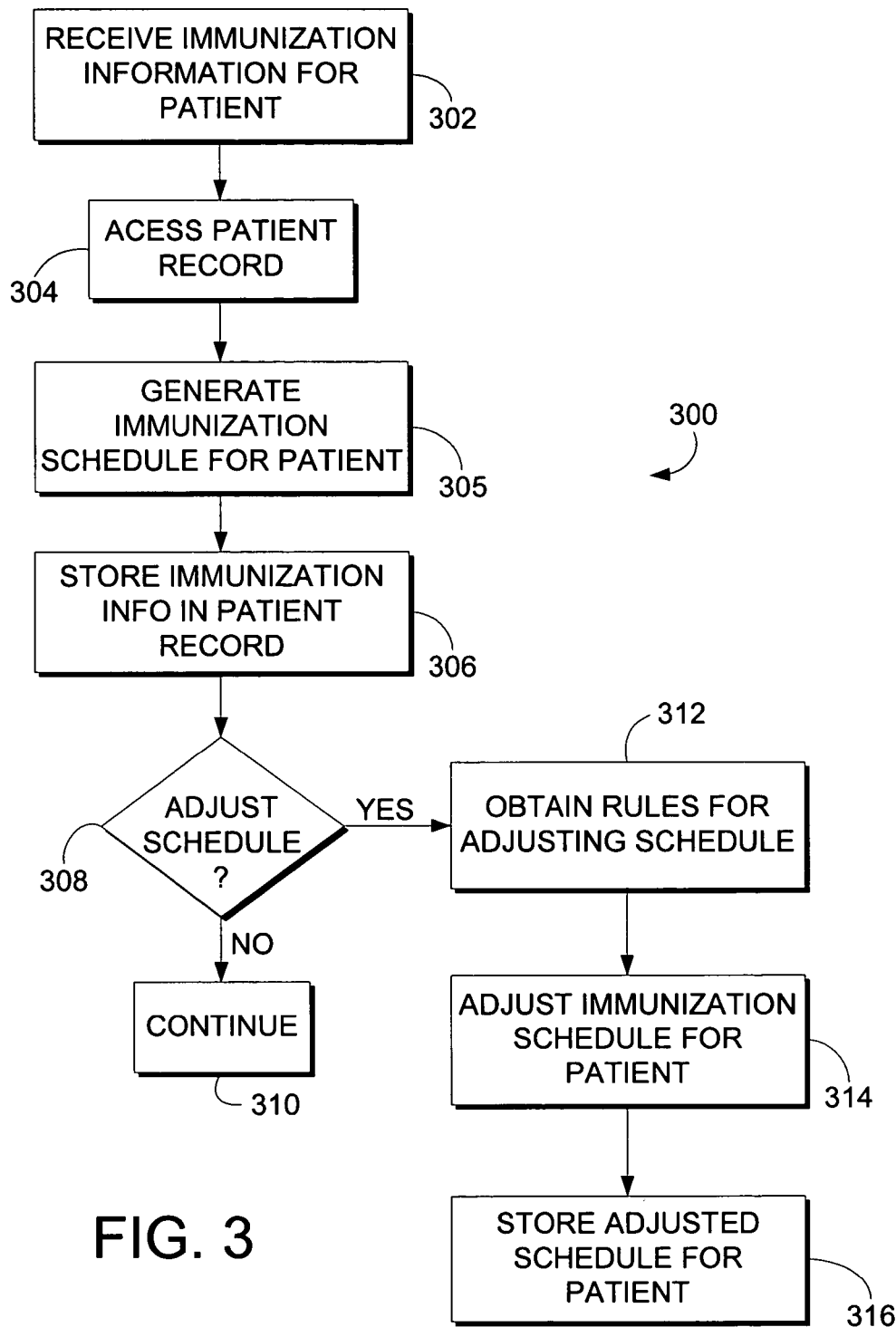
FIG. 3 is a flowchart representative of a computer program for storing an adjusted immunization schedule for a patient in accordance with an embodiment of the present invention.

In still another embodiment, of the present invention, with reference to FIG. 3, a method 300 for storing immunization information for a patient is provided. At block 302 the system receives immunization information for the patient. This information may be entered into the system in any number of ways. For example, information may be entered by a user or may be received from a database. In one embodiment, immunization information is entered into immunization entry screens such as those shown in FIGS. 5-8 and FIGS. 10-13 described below.

At block 304 the system accesses the patient's record. At block 306, the system stores the immunization information received at block 302 in the patient record. At decision block 308, the system determines whether or not the immunization information received for the patient requires an adjustment of the patient's immunization schedule. If not, the system continues to block 310. If so, the system obtains rules for adjusting the schedule at 312.

At block 314, the system adjusts the immunization schedule for the patient accordingly. The system may adjust the immunization schedule of the patient for any number of reasons. For example, if the patient did not receive the immunization due to a refusal by the patient or patient's guardian or because the patient was sick, the user indicates the immunization needs to be rescheduled. Then, the system adjusts the patient's immunizations schedule accordingly. For instance, if the healthcare provider indicates that the immunization should be rescheduled for completion in two weeks because the patient is ill, the system adjusts the patient's immunization schedule to show that an immunization was due two weeks from the date of the patient visit. At block 316, in one embodiment of the invention, the system stores the adjusted immunization schedule for the patient. In another embodiment, the schedule is generated each time the patient record is accessed based on the patient information.

In operation and by way of example, with reference to FIG. 2, the system receives a request for an immunization schedule for fictitious patient John Rakesm at block 202. At block 204 the system obtains information for John Rakesm from his electronic medical record. At block 205 the system obtains the current recommended immunization schedule for infants and adolescents. At block 206 the system generates a customized immunization schedule for John Rakesm based on the patient information received from his electronic medical record and the recommended immunization schedule. At block 208 the system determines that his schedule does not need to be accelerated. Blocks 212 and 222 are bypassed. At block 224 the system displays the customized immunization schedule for John Rakesm.

With reference to FIG. 4, the system displays the customized immunization schedule 400 for patient John Rakesm. The customized immunization schedule 400 includes patient identifying information 402 and the CDC's recommended immunization schedule 404. The CDC's immunization schedule 404 displays the recommended immunizations 406 such as Hepatitis B and the age ranges 408 at which the immunizations are due. For example, according to the exemplary recommended immunization schedule the first dose of Hepatitis B vaccination is due between birth and when the infant is a month and one half old. The customized immunization schedule for the patient also contains immunization history 410 for the patient and a future immunization schedule 412 for the patient.

The future immunization schedule 412 for the patient includes a list 413 of the immunizations to be administered, indications 414 whether each of the vaccines has been contraindicated, the statuses 415 of the immunization and the due dates 416, 418, 420 for each immunization for the first three doses and may include additional dates (not shown) for any other dose that may be due. In this example, the patient's electronic medical record contains no information regarding immunizations for the patient, and the patient's future immunization schedule 412 shows that most of the first dosages of the immunizations are due on Aug. 25, 2003, the date the immunization schedule for the patient was requested. The schedule also includes a chart button 421 and a "ad hoc" button 422. When the chart button 421 is selected, a screen is provided for the user to document details for the immunizations contained on the schedule. By selecting the "ad hoc" button 422, a user is brought to screen where details for immunizations that are not found on the patient schedule can be entered.

Figure 5:
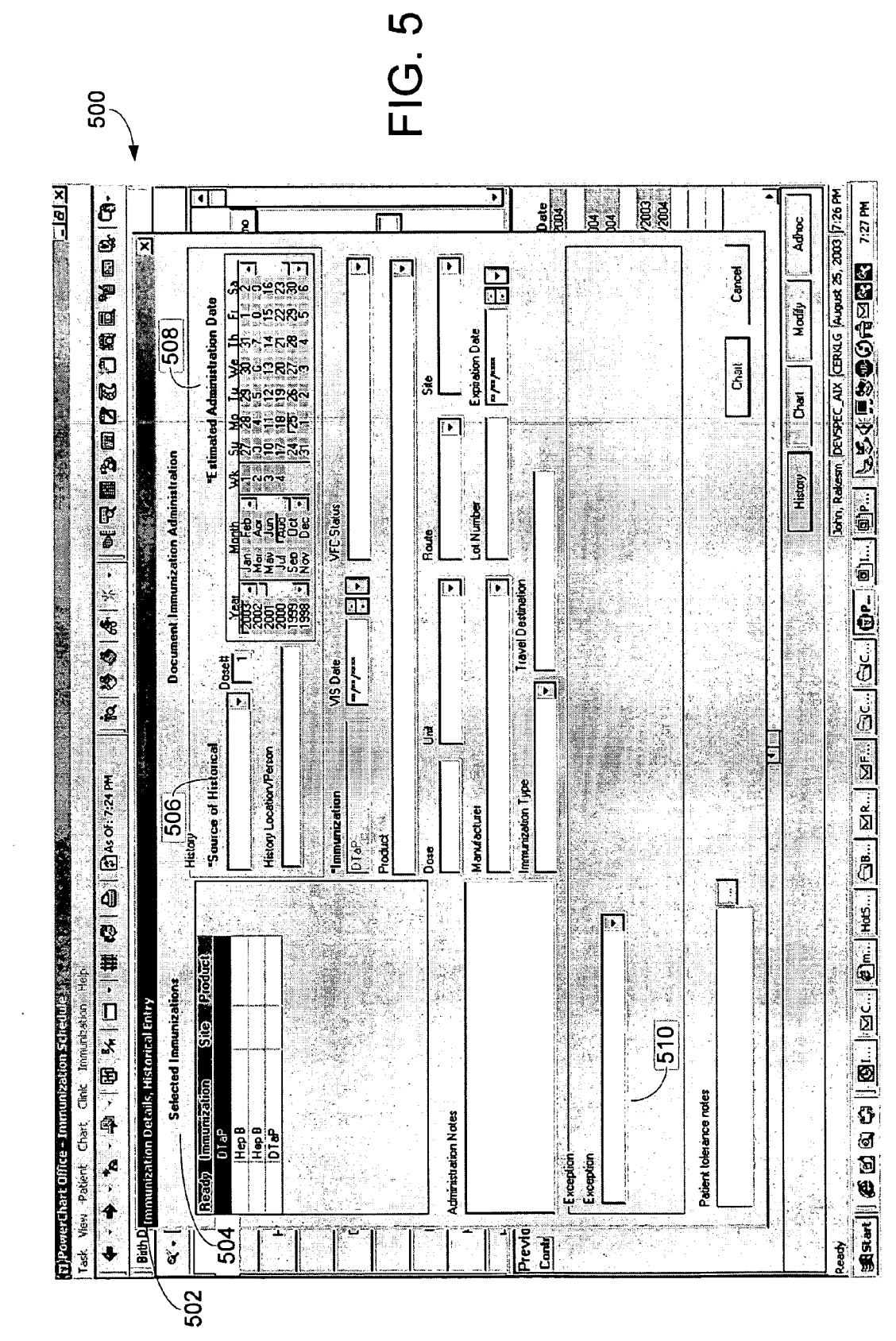

With reference to FIG. 5, an exemplary screen shot 500 for entering historical immunization information for a patient is shown. The screen allows a healthcare provider (or other user) to enter historical details 502 regarding immunizations previously administered to the patient. A user can select the immunization product to be documented from a drop down product menu 504. The user may enter historical information for immunizations provided by other facilities. For example, the healthcare provider could enter historical data from a set of immunizations already given to the patient.

Historical data regarding immunizations can include source information 506 indicating the source of origination for the historical data. Historical data may come from any number of sources. Examples of sources include historical data from an immunization card carried by the parents. Another example is the recollection of a parent of the patient.

The system will also allow the user to enter an estimated administration date 508. Other historical data that may be recorded about immunizations previously received by the patient include the location/person who administered the immunization, the Vaccine Information Sheet (VIS) date, the Vaccine for Children (VFC) status, the product, the dose, the unit, the route, the site, the manufacturer, the lot number the expiration date, the immunization type and a travel destination.

VIS is an information sheet provided under Federal Law to parents of children receiving immunizations. The VIS information entered by the user is the date of the version of the sheet provided to the parents. VFC is a program that allows healthcare organizations to be reimbursed for some immunizations given to qualified patient. The system allows the user to record information regarding whether a patient qualifies under VFC and can track and report this information for reimbursement purposes. The historical entry screen may also include an entry field 510 for entering information regarding whether or not the patient tolerated the immunization or whether they experienced any adverse reactions.

Figure 6:
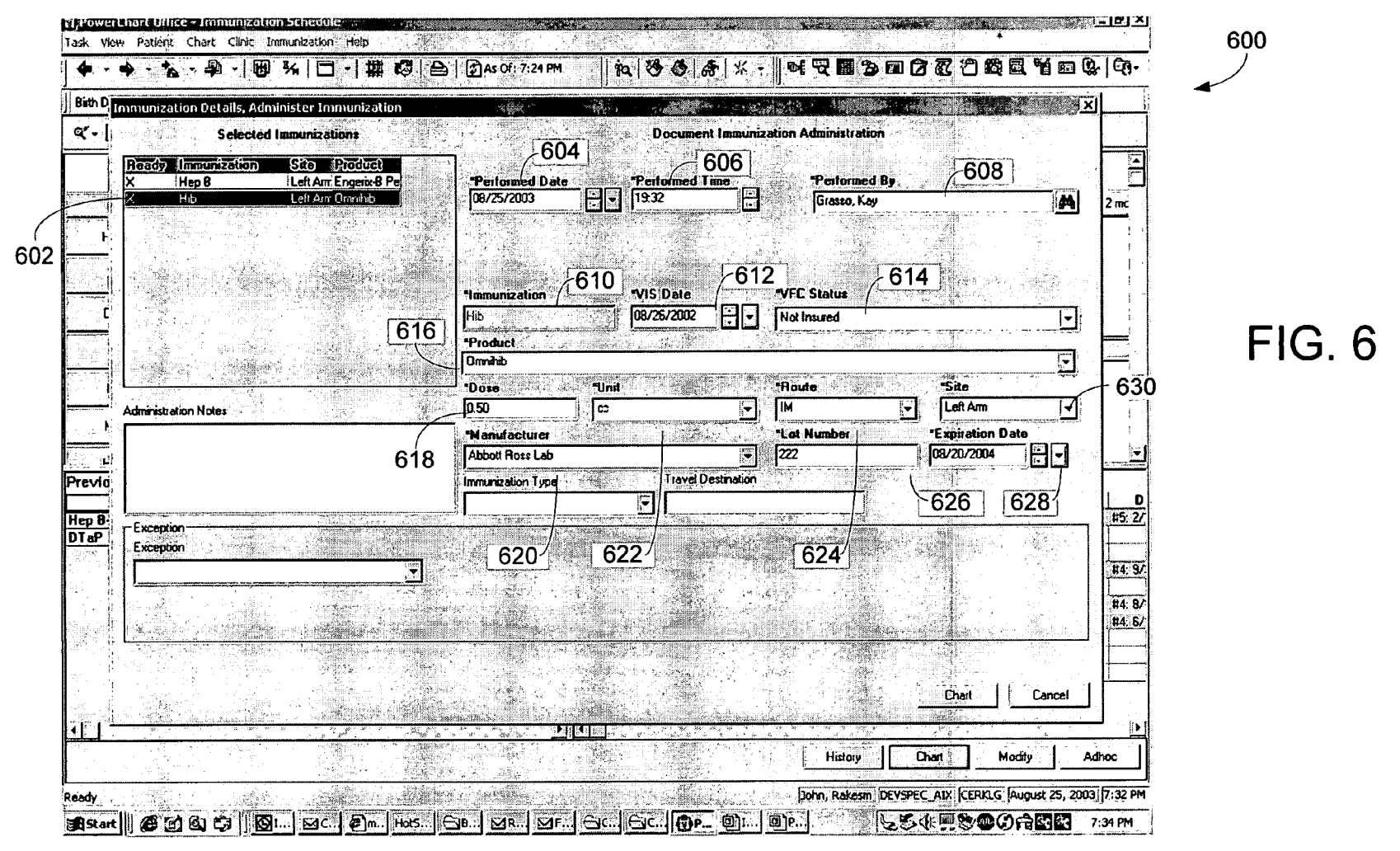

With reference to FIG. 6, another exemplary screen shot 600 for entering administration immunization information for a patient is shown. The screen allows a healthcare provider to enter details regarding immunizations to be administered to the patient. A user can select the immunization to be documented from a drop down immunization menu 602. Other details that may be documented include the date performed 604, the time performed 606, the name 608 of the provider administering the immunization. Other information may be the VIS date 612, the VFC status 614, the product 616, the dose 618, the unit 622, route 624, site 630 manufacturer 620, lot number 626 and expiration date 628. Any other details pertinent to the immunization may also be entered in the "Administration note" section. Once this information is entered into the system it is stored in the patient's electronic medical record and/or other database/table for later use.

The immunization details entered into the screen 600 are for the Hib immunization as indicated at 602, 610. The performed date 604 was Aug. 25, 2003 and time 606 was 19:32 by a healthcare provider Kay Grasso 608. The VIS date 612 was Aug. 26, 2003 and the VFC status 614 of the patient was uninsured. The dosage 618 was 0.5 and the unit 622 was in cubic centimeters or cc. The route 624 was intramuscular and the site 630 was in the left arm. The manufacturer 620 of the immunization was Abbott Ross Lab with a lot number 624 of "222" and an expiration date 628 of Aug. 20, 2004. This information is then stored in the patient's electronic medical record and/or some other database and/or table.

Figure 7:
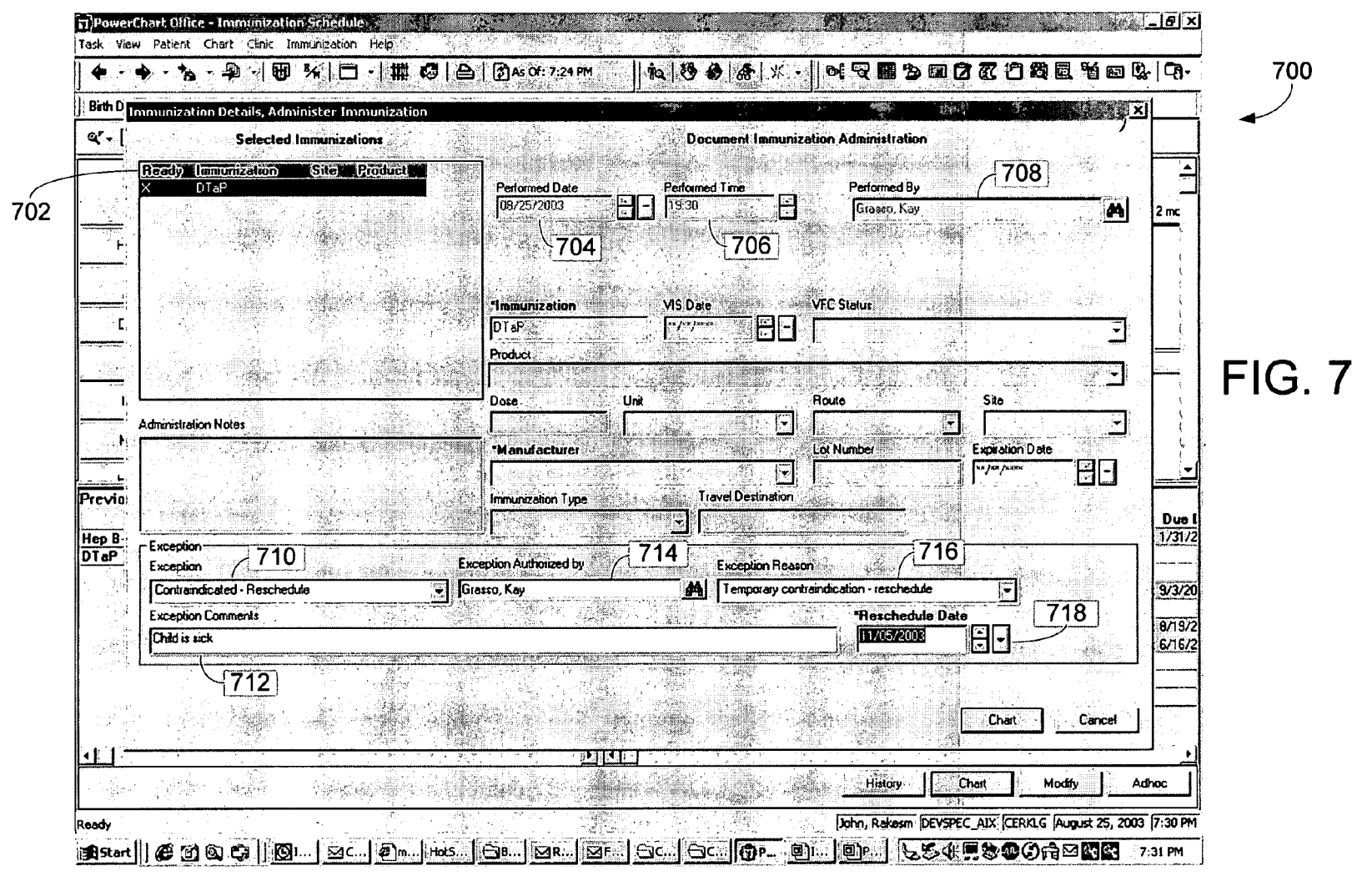

With reference to FIG. 7 an exemplary screen shot 700 for entering exceptions to administration immunization information for a patient is shown. The screen shows that there is an exception to the "DTaP" to be performed on Aug. 25, 2003 (704) at 19:30 (706) by fictitious healthcare provider Kay Grasso (708). The child was sick the immunization will not be performed that date and will be rescheduled. This information is entered into the exception field 710 of FIG. 7. Other fields for exceptions include an authorization field 714, an exception reason field 716, exception comment field 712 for explaining the exception and a reschedule date field 718 for rescheduling the immunization. As can be seen in FIG. 7 the DTaP immunization for the child will be rescheduled because the child is sick and will be rescheduled for Nov. 5, 2003. This information is stored in the patient's electronic medical record or other table and/or database.

Figure 8:
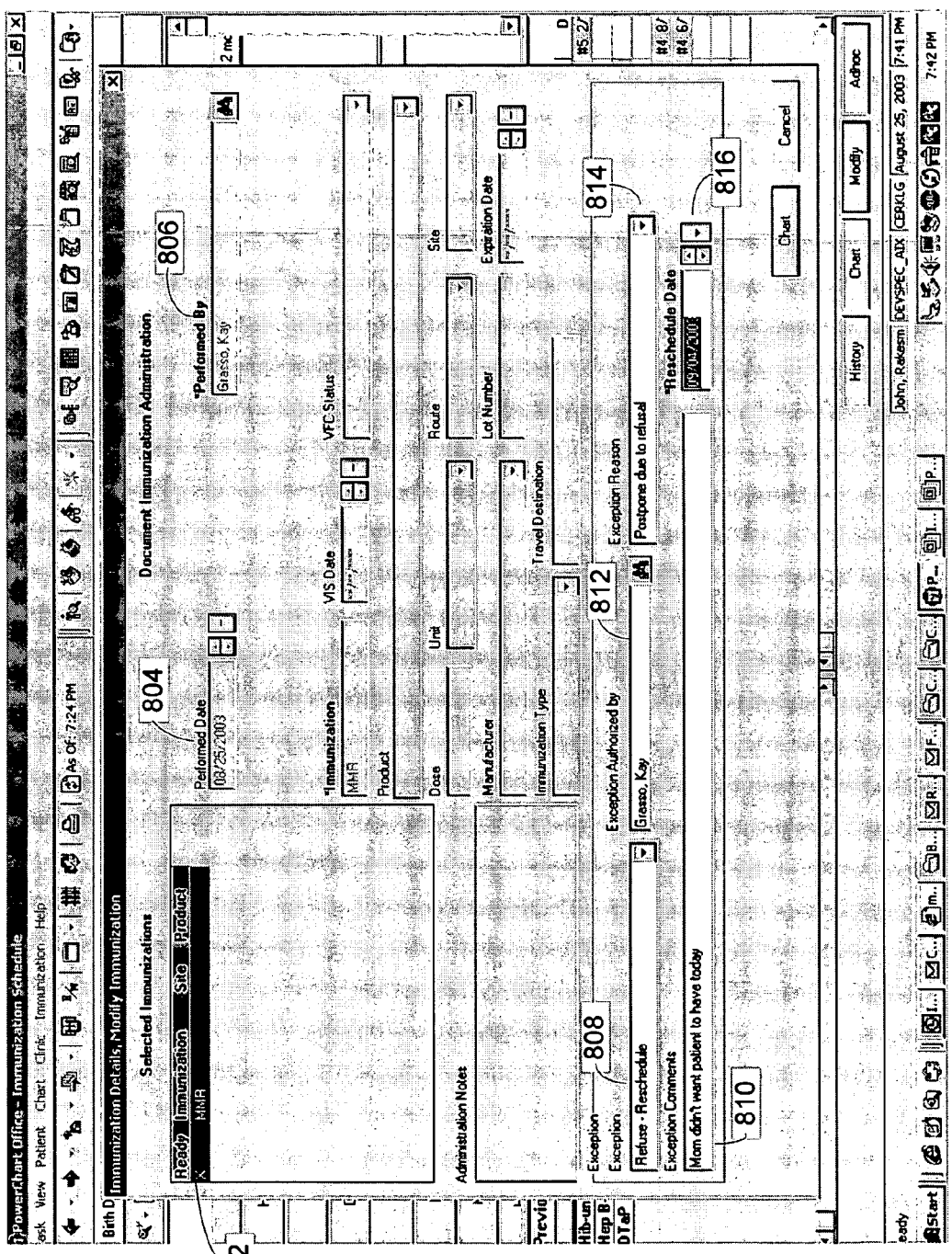
Figure 10:
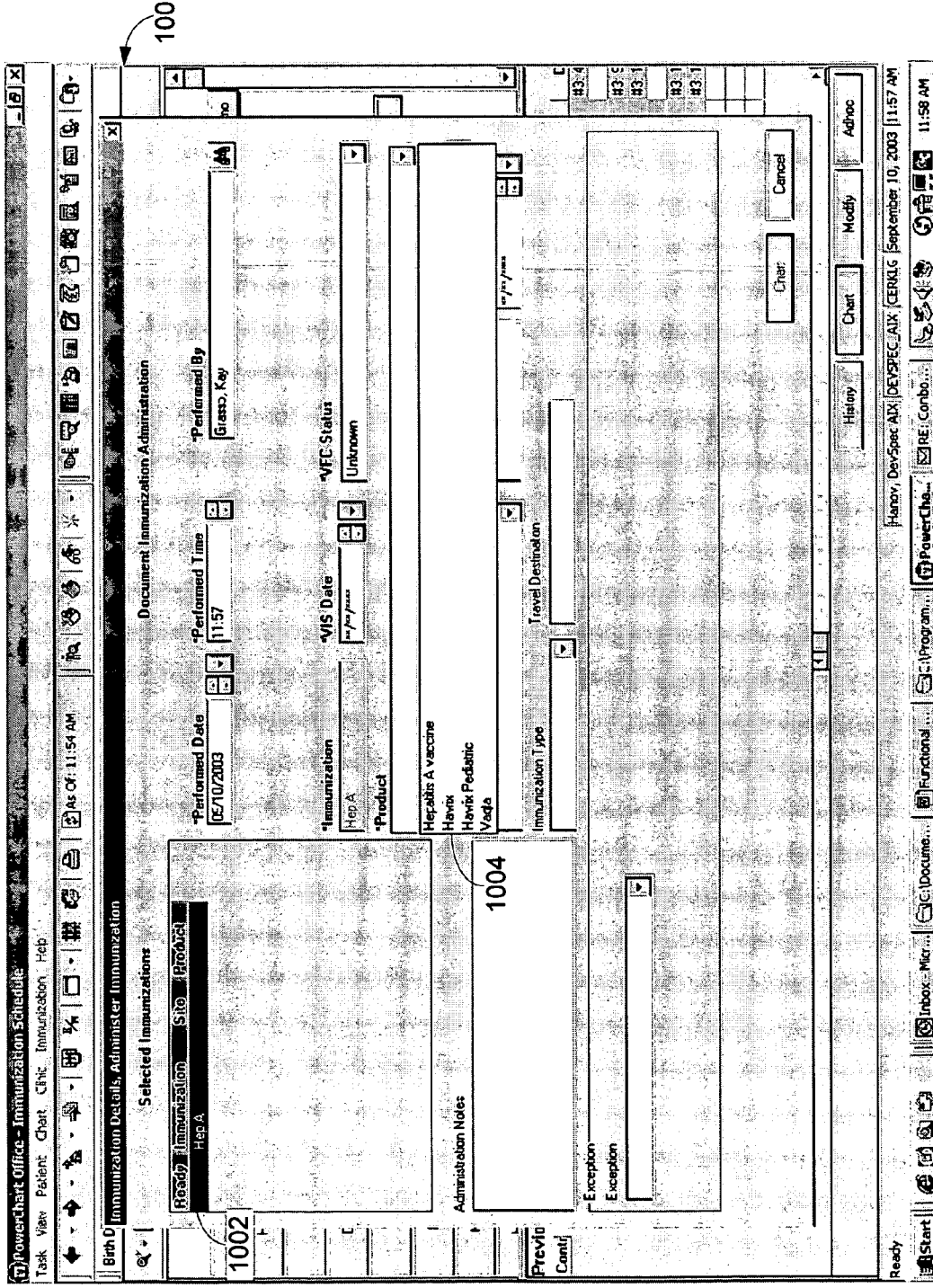
FIGS. 10-13 illustrate additional screenshots for entering immunization information in accordance with an embodiment of the invention.

With reference to FIG. 8, an exemplary screen shot 800 for entering exceptions to administration immunization information for a patient is shown. An exception to an MMR immunization (802) to be performed on Aug. 25, 2003 (704) at 19:30 (804) by fictitious healthcare provider Kay Grasso (806). The patient's mother did not want the patient to receive the MMR immunization so it will not be performed and will be rescheduled. The information is entered into the system. For example, the refusal is entered into the exception field 808. Other information is entered into the fields for exceptions include an authorization field 812, an exception reason field 814, exception comment field 810 for explaining the exception and a reschedule date field 816 for rescheduling the immunization. As can be seen in FIG. 8 the MMR immunization for the child will be rescheduled for Sep. 4, 2003 because the mother did not want the patient to have the MMR immunization that day. This information is stored in the patient's electronic medical record or other table and/or database.

With reference to FIG. 9, the system displays the customized immunization schedule 900 for patient John Rakesm (identified at 902) based on information from his electronic medical record and the recommended immunization schedule. The customized immunization schedule 900 now includes information regarding the patient's previous immunizations 904 for the Hib 906, Hepatitis B 908 and DTaP 910 immunizations.

The system also displays a future immunization schedule 912 for the patient. The future immunization schedule includes a vaccine list 914, details 916 as to whether the vaccine was contraindicated 916, the statuses 918 of the immunizations, and the due dates 920, 922, 914 for the different dosages of the immunizations. The system displays that the patient received the first dosage of a Hib immunization on Aug. 25, 2003 as was entered in FIG. 6. The system also shows displays that the second dose of DTaP was rescheduled for Nov. 5, 2003 as was entered into the system in FIG. 7. The system also displays that the first dose of MMR was rescheduled for Sep. 4, 2003 as was entered into the system in FIG. 8.

With reference to FIGS. 10-13, the system also provides an exemplary screen for entering information for combination immunizations. For instance, with reference to FIG. 10, an exemplary screen shot 1000 of the implementation of recording administration immunization information for single immunization is shown. The user has selected Hepatitis A as the immunization 1002 to be administered. The system automatically provides a list 1004 of products for the Hepatitis A immunization. The list includes: Hepatitis A vaccine, Havrix, Havrix Pediatric and Vaqta. The system obtains the list of products for a particular immunization from a database and/or table.

Figure 11:
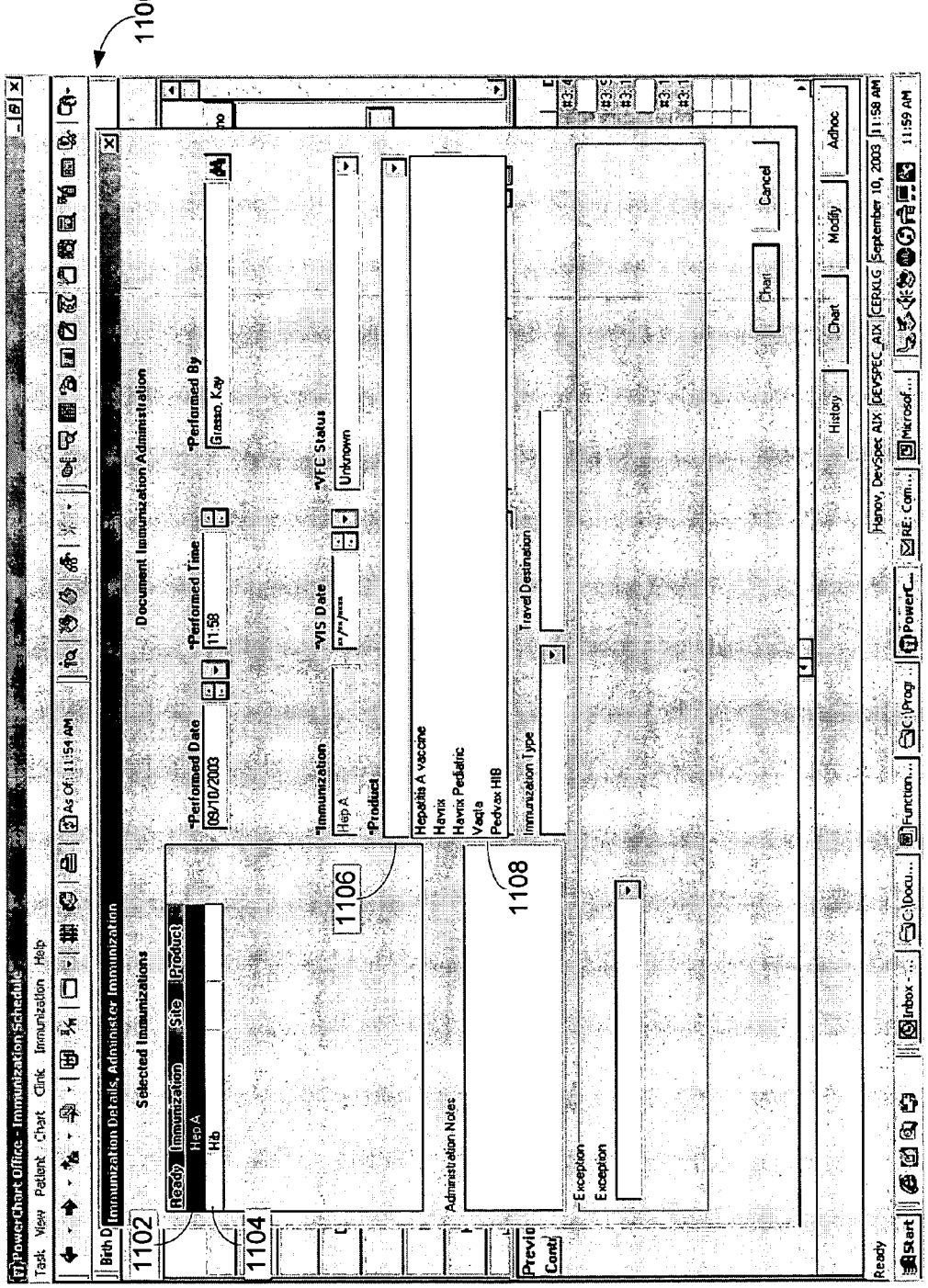
Figure 12:
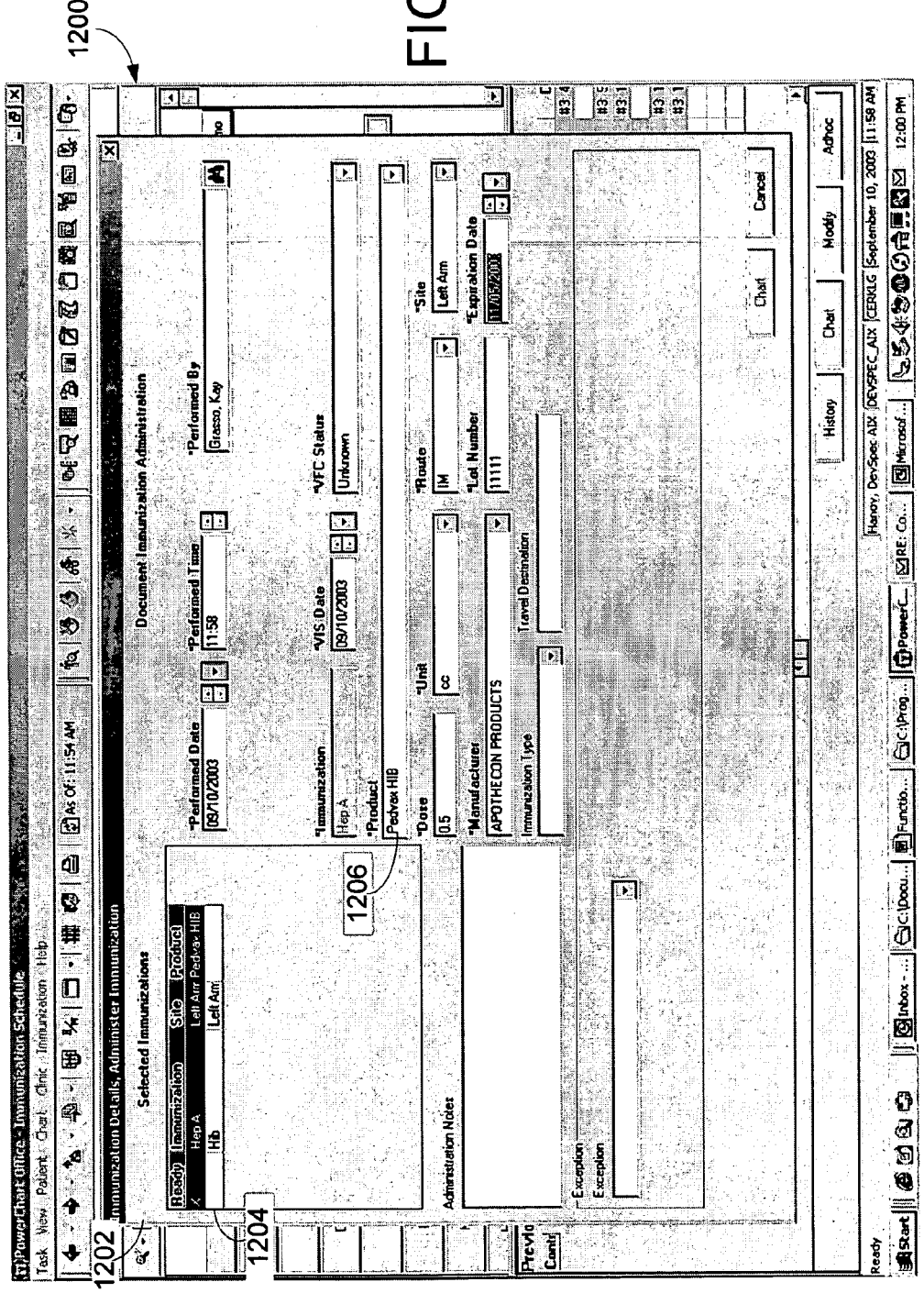
Figure 13:
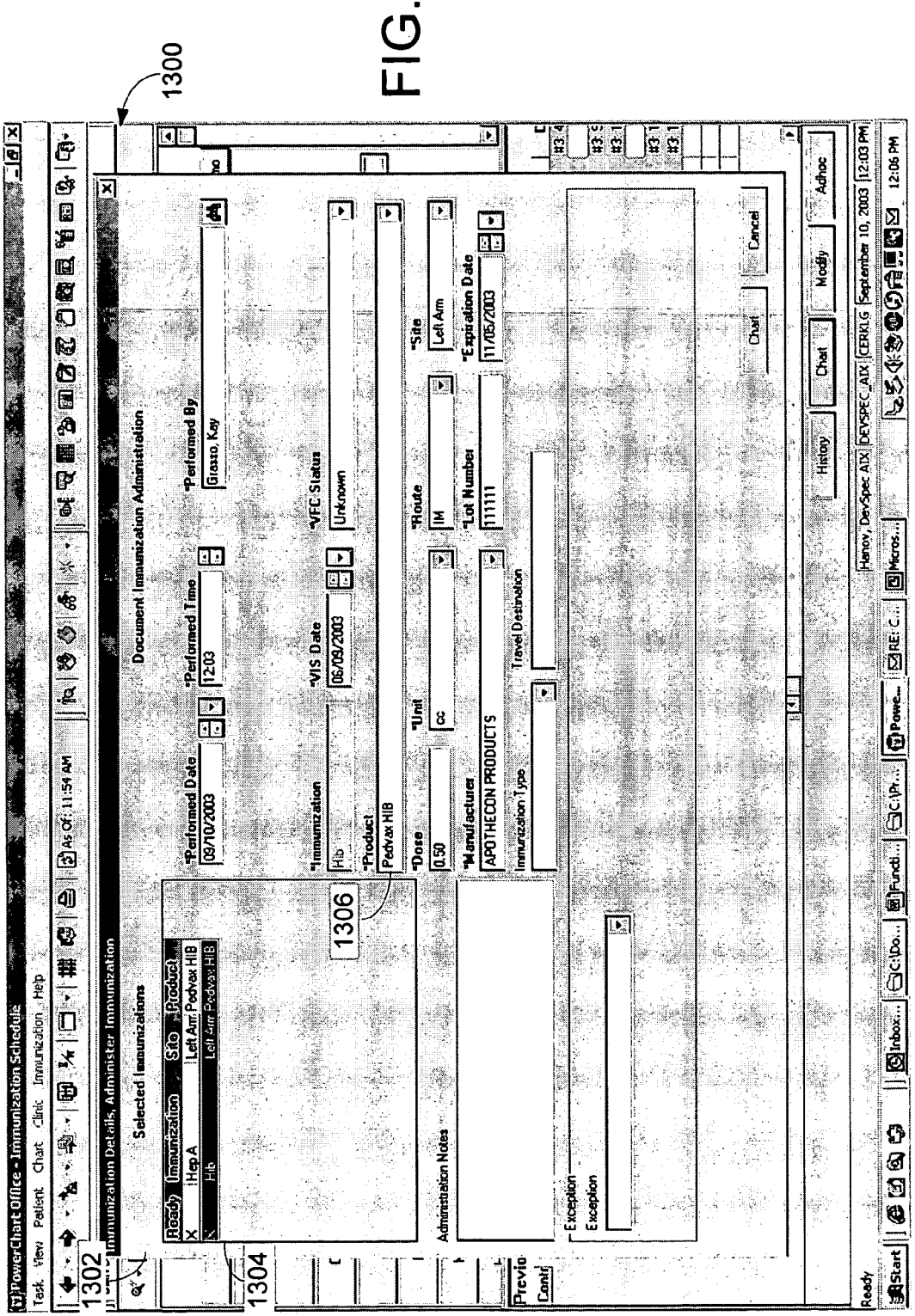

With reference FIG. 11, an exemplary screen shot 1100 of the user's selection of Hib 1104 as another immunization to be administered to the patient in addition to the Hepatitis A 1102 immunization is shown. The system automatically adds Pedvax HIB 1108 to the list of products 1106 that may be administered to the patient because it satisfies both the Hepatitis A and Hib immunizations. With reference to FIG. 12 and FIG. 13, exemplary screen shots 1200 and 1300 for recording the immunization information for a combination immunization are shown. In FIG. 12, the combination immunization Pedvax HIB 1206 is recorded for the Hepatitis A immunization 1202 to be administered to the patient. In FIG. 13, the combination immunization Pedvax HIB 1306 is also recorded for the Hib immunization 1306 to be administered to the patient. The system of the present invention also allows the user to record combination immunization information for separate immunizations.

The present invention provides a method and system in a computerized environment for storing and displaying patient immunization information. Although the invention has been described with reference to the preferred embodiment illustrating the attached drawing figures, it was noted that substitutions may be made and equivalents employed here and without departing from the scope of the invention as recited in the claims. For example, additional substance may be added and substance submitted without departing from the scope of the invention.

The invention claimed is:

1. A computer-implemented method in a computer system for preventing one or more immunizations from being administered to a person too early, the method comprising:
   receiving from a clinician, utilizing a first computer process, a request for an immunization schedule for a person during a present clinical visit;
   receiving from the clinician, utilizing a second computer process, an identification of an immunization to be administered to the person, wherein the identification of the immunization is input by the clinician during the present clinical visit with the person;
   generating, utilizing a third computer process, a custom immunization schedule for the person, wherein the custom immunization schedule is based on at least one immunization administered to the person during at least one former clinical visit prior to the present clinical visit, the immunization identified from the input by the clinician to be administered to the person during the present clinical visit, and a standard schedule of recommended immunizations;
   in response to receiving the identification of the immunization to be administered during the present clinical visit, determining, utilizing a fourth computer process, whether it is too soon to administer the immunization, wherein the determination whether it is too soon to administer the immunization is based on the custom immunization schedule for the person;
   based on a determination that it is not too soon to administer the immunization, displaying a notification that is it safe to administer the immunization during the present clinical visit;
   based on a determination that it is too soon to administer the immunization, displaying a warning that the immunization is being administered too soon; and
   updating the custom immunization schedule for the person in response to receiving an input regarding the immunization to be administered during the present clinical visit,
   wherein the first, second, third and fourth computer processes are executed utilizing one or more computing devices.

2. The method of claim 1, further comprising:
   upon determining that it is too soon to administer the immunization, determining it is still safe to administer the immunization.

3. The method of claim 2, further comprising:
   based on a determination that it is still safe to administer the immunization, outputting information that it is safe to administer the immunization.

4. The method of claim 2, further comprising:
   upon determining that it is too soon to administer the immunization, determining that it is not safe to administer the immunization; and
   based on a determination that it is not safe to administer the immunization, outputting information that it is not safe to administer the immunization.

5. The method of claim 1, further comprising:
   obtaining information regarding the safe timing of immunizations from a database.

6. The method of claim 5, further comprising:
   obtaining information from an electronic medical record of the person stored within a comprehensive healthcare system.

7. The method of claim 6, further comprising:
   utilizing the information from the electronic medical record of the person and the information regarding safe timing of immunizations to determine whether an immunization is being administered too soon.

8. A computer system including one or more computer-readable storage media having computer-executable modules stored thereon for preventing one or more immunizations from being administered to a person too early, the computer-executable modules comprising:
   a receiving module for receiving from a clinician an identification of an immunization to be administered to a person during a present clinical visit, wherein the identification of the immunization is received from the clinician during the present clinical visit;
   a determining module for determining whether it is too soon to administer the immunization in response to receiving the identification of the immunization to be administered from the clinician during the present clinical visit, wherein determining whether it is too soon to administer the immunization includes accessing a custom immunization schedule for the person that was generated based on at least one immunization administered to the person during at least one former clinical visit prior to the present clinical visit, the immunization identified from the input by the clinician to be administered to the person during the present clinical visit, and a standard schedule of recommended immunizations;
   a displaying module for displaying a warning that the immunization is being administered too soon or a notification that the immunization may be administered; and
   an updating module for updating the custom immunization schedule for the person in response to receiving an input regarding the immunization to be administered during the present clinical visit.

9. The system of claim 8, further comprising:
   a second determining module for determining whether it is still safe to administer the immunization even though it is too soon to administer the immunization.

10. The system of claim 9, wherein if it is safe to administer the immunization, outputting information that it is safe to administer the immunization.

11. The system of claim 9, wherein if it is not safe to administer the immunization, outputting information that it is not safe to administer the immunization.

12. A computer-storage medium having computer-executable instructions for performing a method for preventing one or more immunizations from being administered to a person too early, the method comprising:
   receiving from a clinician, a request for an immunization schedule for a person during a present clinical visit;
   receiving from the clinician an identification of an immunization to be administered to the person, wherein the identification of the immunization is input by the clinician during the present clinical visit with the person;
   generating a custom immunization schedule for the person, wherein the custom immunization schedule is based on at least one immunization administered to the person during at least one former clinical visit prior to the present clinical visit, the immunization identified from the input by the clinician to be administered to the person during the present clinical visit, and a standard schedule of recommended immunizations;

in response to receiving the identification of the immunization to be administered to the person during the present clinical visit, determining whether it is too soon to administer the immunization during the present clinical visit based on the custom immunization schedule;

based on a determination that it is too soon to administer the immunization, determining whether it is safe to administer the immunization too soon;

upon determining that it is not safe to administer the immunization too soon, displaying a warning indicating that the immunization is not safe to administer to the person wherein the warning is a first popup warning window;

upon determining that it is safe to administer the immunization too soon, notifying the clinician that it is safe to administer the immunization too soon;

based on a determination this it is not too soon to administer the immunization, determining whether the immunization will cause an adverse reaction to the person;

upon determining that the immunization will cause an adverse reaction, displaying a warning that the immunization will cause an adverse reaction via a second popup warning window;

upon determining that the immunization will not cause an adverse reaction, displaying a message that the immunization may be administered during the present clinical visit; and updating the custom immunization schedule for the person in response to receiving an input regarding the immunization to be administered during the present clinical visit.

13. The computer-storage medium of claim 12, further comprising:
    obtaining healthcare information for the person from the person's electronic medical record.

14. The computer-storage medium of claim 12, further comprising:
    obtaining information regarding adverse reactions and immunizations.

15. The computer-storage medium of claim 14, further comprising:
    comparing the information regarding adverse reactions to the information for the person obtained from the person's electronic medical record.

16. The computer-storage medium of claim 15, wherein the information obtained from the person's electronic medical record includes medications being taken.

17. The computer-storage medium of claim 15, wherein the information obtained from the person's electronic medical record includes allergy information.

18. The computer-storage medium of claim 15, wherein the information obtained from the person's electronic medical record includes a medical condition that can cause adverse reactions to the immunization.

19. The computer-storage medium of claim 15, wherein the information obtained from the person's electronic medical record includes a genetic condition that predisposes the person to adverse reactions to the immunizations.

* * * * *